(12) United States Patent
Mihara

(10) Patent No.: US 9,907,506 B2
(45) Date of Patent: Mar. 6, 2018

(54) DEVICES AND METHODS FOR MEASURING SKIN MOISTURE

(71) Applicant: Empire Technology Development LLC, Wilmington, DE (US)

(72) Inventor: Masaaki Mihara, Chiba (JP)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 912 days.

(21) Appl. No.: 14/284,579

(22) Filed: May 22, 2014

(65) Prior Publication Data

US 2015/0335279 A1    Nov. 26, 2015

(51) Int. Cl.
*A61B 5/00* (2006.01)
*A61B 5/053* (2006.01)
*A61B 10/00* (2006.01)

(52) U.S. Cl.
CPC ............ *A61B 5/443* (2013.01); *A61B 5/0537* (2013.01); *A61B 5/4266* (2013.01); *A61B 10/0064* (2013.01); *A61B 2562/029* (2013.01)

(58) Field of Classification Search
CPC ... A61B 5/443; A61B 5/14517; A61B 5/4266; A61B 510/0064
See application file for complete search history.

(56) References Cited

U.S. PATENT DOCUMENTS

| | | | |
|---|---|---|---|
| 6,439,028 B1 | 8/2002 | Imhof | |
| 2004/0012912 A1* | 1/2004 | Rombach | G01N 27/223 361/321.6 |
| 2008/0022935 A1* | 1/2008 | Fine | A01K 1/0353 119/28.5 |

FOREIGN PATENT DOCUMENTS

| | | |
|---|---|---|
| JP | 2001-204693 A | 7/2001 |
| JP | 2006-198321 A | 8/2006 |
| JP | 2014-014425 A | 1/2014 |

OTHER PUBLICATIONS

"iOS / Android for a headphone jack accessory type skin moisture meter-easily at or on the go-home," accessed at http://www.itaccess.co.jp/products/smartskincare/moisture_checker/index.html, accessed on May 15, 2014, pp. 1-4.

(Continued)

*Primary Examiner* — Christian Jang
(74) *Attorney, Agent, or Firm* — Maschoff Brennan

(57) ABSTRACT

Technologies are generally described for measuring skin moisture using a skin moisture measuring device. Example devices and systems described herein may include one or more of an elongated enclosure, an inlet, a moisture sensor, and/or a cooling unit. The inlet may be arranged at a first end of the elongated enclosure, and may be configured to be in contact with skin and receive moisture transpiring from the skin. The moisture sensor may be arranged between the first end and a second end inside the elongated enclosure, and configured to detect an amount of the moisture. Further, the cooling unit may be arranged at the second end of the elongated enclosure, and configured to cool and condense the moisture. The cooling unit may be controlled to maintain a substantially constant temperature difference between a first temperature proximate the moisture sensor and a second temperature proximate the cooling unit.

26 Claims, 18 Drawing Sheets

(56) References Cited

OTHER PUBLICATIONS

Mündlein, M., et al., "Transepidermal Water Loss (TEWL) Measurements With Two Novel Sensors Based on Different Sensing Principles," Proceedings Eurosensors, vol. I, pp. 5 (2006).

Sahta, I., et al., "Thermoregulatory System019s Integrated in the Clothes Effect on the Human Microclimate," In 150 Years of Research and Innovation in Textile Science : 11th World Textile Conference (AUTEX 2011): Book of Proceedings, pp. 856-860 (2011).

* cited by examiner

HUMIDITY OF CHEEK

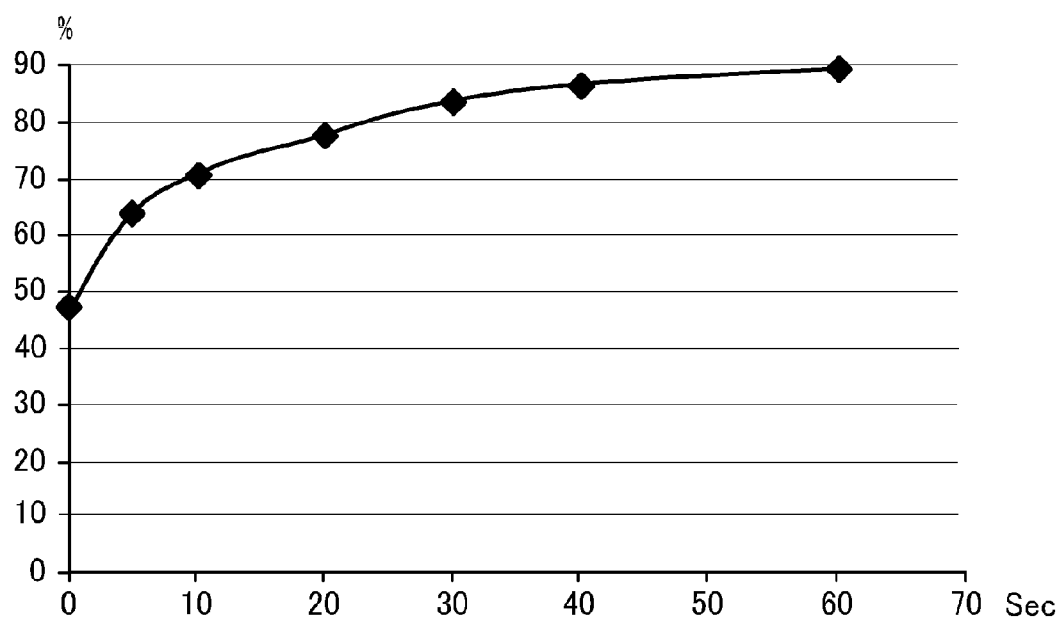

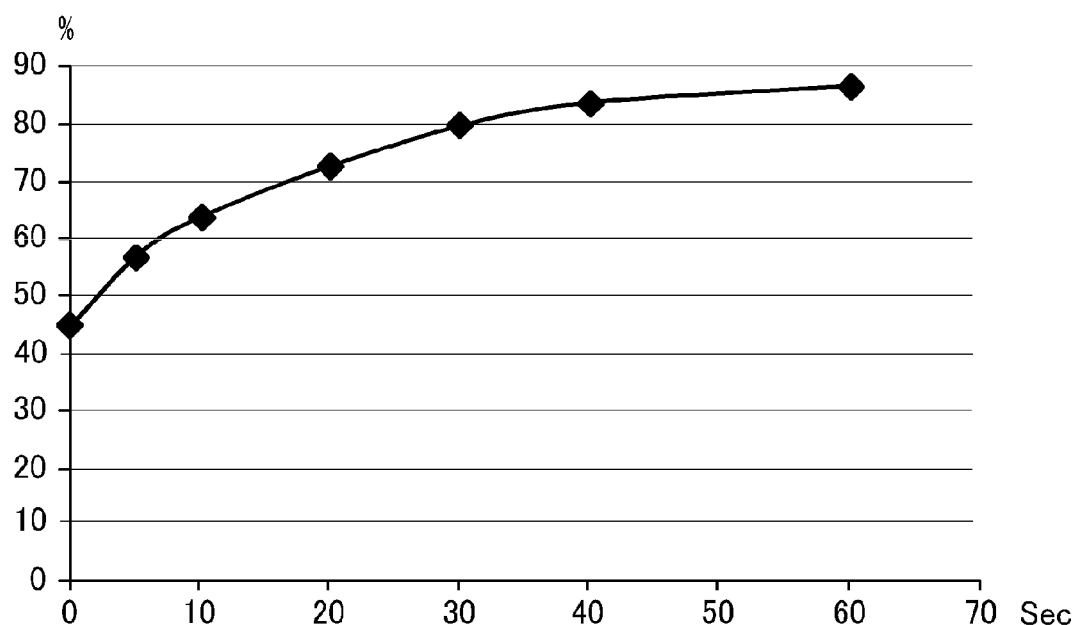

DEVICES AND METHODS FOR MEASURING SKIN MOISTURE

BACKGROUND

Unless otherwise indicated herein, the approaches described in this section are not prior art to the claims in this application and are not admitted to be prior art by inclusion in this section.

Human or animal skin is hygroscopic and permeable, such that water passes from inside a body through skin to the surrounding atmosphere via diffusion and evaporation or skin can absorb moisture from the surrounding atmosphere. The hygroscopic property of skin determines the health and cosmetic problems of the skin because the capability of skin for retaining moisture can be deteriorated when it is damaged through exposure to skin cosmetic products and exposure to ultraviolet radiation from the sun. Accordingly, it is important to precisely measure skin moisture content or hydration level to determine the overall health of skin or moisture content in skin so that one can assess possible cosmetic options and skin care options to maintain or improve the health of the skin. Also, the hydration measurement will be desirable for all cosmetic applications including formulation, support of efficacy claim and efficacy testing of skin care products.

Skin moisture measuring devices have been developed to detect the hydration level in skin, and have employed various techniques. One example method measures capacitance of a dielectric medium. This method measures the change in dielectric constant due to skin surface hydration changing the capacitance of a precision capacitor. The capacitance measurement can be conducted in a short period of time and may not be influenced by substances in the skin (for example, salts or residues of topical applied products). However, such measurement is conducted by using electrodes or probes attached to skin, which may impose stress on the skin. Further, although this method provides decent precision of moisture measurement, it is costly and may not be implemented in a portable size for individual users.

SUMMARY

Technologies generally described herein relate to measuring moisture in skin.

In some examples, a device configured to measure skin moisture described herein may include an elongated enclosure, an inlet, a moisture sensor, and a cooling unit. The elongated enclosure may have a first end and a second end. The inlet may be arranged at the first end of the elongated enclosure, and may be configured to be in contact with skin and to receive moisture transpiring from the skin. The moisture sensor may be arranged between the first end and the second end inside the elongated enclosure, and may be configured to detect an amount of the moisture. The cooling unit may be arranged at the second end of the elongated enclosure, and may be configured to cool and condense the moisture.

In some examples, methods of measuring skin moisture are described. Example methods may include receiving moisture transpiring from skin through an inlet arranged at a first end of an elongated enclosure of a skin moisture measuring device. An amount of the moisture may be detected by a moisture sensor arranged between the first end and a second opposite end inside the elongated enclosure. The moisture may be cooled and condensed by a cooling unit arranged at the second end of the elongated enclosure.

In some examples, a computer-readable storage medium is described that may be adapted to store a program operable by a skin moisture measuring device. The skin moisture measuring device may include various features as further described herein. The program may include one or more instructions for receiving moisture transpiring from skin through an inlet arranged at a first end of an elongated enclosure of a skin moisture measuring device, and detecting an amount of the moisture by a moisture sensor arranged between the first end and a second opposite end inside the elongated enclosure. The program may further include one or more instructions for cooling and condensing the moisture by a cooling unit arranged at the second end of the elongated enclosure.

In some examples, methods of manufacturing a skin moisture measuring device are described. Example methods may include preparing an elongated enclosure having a first end, a second end and an inlet arranged at the first end, where the inlet may be configured to be in contact with skin and to receive moisture transpiring from the skin. A moisture sensor may be disposed between the first end and the second end inside the elongated enclosure, where the moisture sensor may be configured to detect an amount of the moisture. A cooling unit may be disposed at the second end, where the cooling unit may be configured to cool and condense the moisture.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIGS. 11A to 11D illustrate graphs showing humidity of cheek and forehead in dry and normal conditions, respectively, which were measured by a skin moisture measuring device, all arranged in accordance with at least some embodiments described herein.

DETAILED DESCRIPTION

Figure 1:
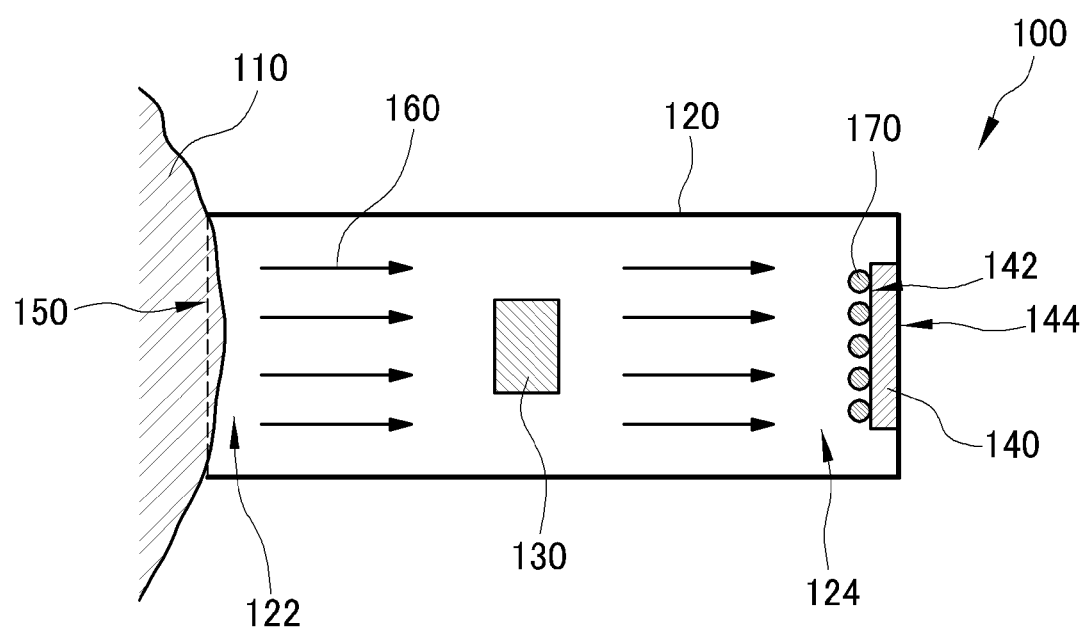
FIG. 1 schematically shows a diagram of an example skin moisture measuring device configured to measure moisture transpiring from skin.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, among other things, to methods, apparatus, systems, devices and computer program products related to measuring moisture in skin.

Briefly stated, technologies are generally described for measuring skin moisture using a skin moisture measuring device. Example devices and systems described herein may include one or more of an elongated enclosure, an inlet, a moisture sensor, and/or a cooling unit. The cooling unit can for example be a thermoelectric cooler. The inlet may be arranged at a first end of the elongated enclosure, and may be configured to be in contact with skin and to receive moisture transpiring from the skin. The moisture sensor may be arranged between the first end and a second end inside the elongated enclosure, and may be configured to detect an amount of the moisture. The detected amount of moisture may indicate an extent of moisture loss from the skin or a condition of the skin barrier function. Further, the cooling unit may be arranged at the second end of the elongated enclosure, and may be configured to cool and condense the moisture. In some embodiments, a first temperature of an atmosphere adjacent to the moisture sensor and a second temperature of an atmosphere adjacent to the cooling unit may be detected. Also, in response to the detected first and second temperatures, the cooling unit may be controlled to maintain a substantially constant temperature difference between the first temperature and the second temperature.

FIG. 1 schematically shows a diagram of an example skin moisture measuring device configured to measure moisture transpiring from skin, arranged in accordance with at least some embodiments described herein. As depicted, a skin moisture measuring device 100 may include one or more of an elongated enclosure 120, a moisture sensor 130, and/or a cooling unit 140.

In some embodiments, elongated enclosure 120 may have a first end 122 at which an inlet 150 may be arranged and configured to be in contact with skin 110. Further, elongated enclosure 120 may have a second end 124 opposite first end 122 at which cooling unit 140 may be arranged. Moisture sensor 130 may be arranged between first end 122 and second end 124 inside elongated enclosure 120.

In operation, inlet 150 may be configured to receive moisture 160 transpiring from skin 110. Moisture 160 transpiring from skin 110 may flow in a direction from skin 110 to cooling unit 140 because there is a temperature gradient between skin 110 and cooling unit 140 which has a lower temperature than skin 110. In the meantime, moisture sensor 130 may detect an amount of moisture 160 that is flowing through or near moisture sensor 130. Further, cooling unit 140 may be configured to cool and condense moisture 160 (as indicated with 170 in FIG. 1) that is reaching a surface of cooling unit 140 facing moisture sensor 130.

In some embodiments, a first temperature of an atmosphere adjacent to moisture sensor 130 may be detected while a second temperature of an atmosphere adjacent to cooling unit 140 may be detected. In response to detecting the first and second temperatures, cooling unit 140 may be controlled to maintain a substantially constant temperature difference (or gradient) between the first and second temperatures. For example, cooling unit 140 may be a thermoelectric cooler, such as Peltier cooler, configured to transfer heat from a second surface 142 of cooling unit 140 facing moisture sensor 130 to a first surface 144 of cooling unit 140 such that second surface 142 becomes cooler than first surface 144. In this configuration, the amount of moisture measured by moisture sensor 130 may change depending on the rate of moisture transpiration at skin 110.

In some embodiments, the amount of moisture detected by moisture sensor 130 may indicate an extent of moisture loss from skin 110. In some other embodiments, the amount of moisture detected by moisture sensor 130 may indicate a condition of the skin barrier function.

Figure 2:
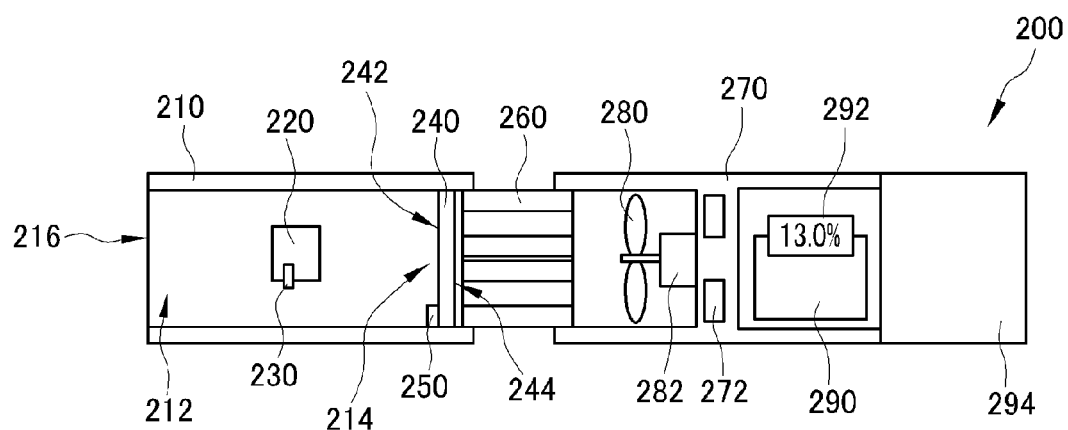
FIG. 2 schematically shows a block diagram of another example skin moisture measuring device configured to measure moisture transpiring from skin.
Figure 3:
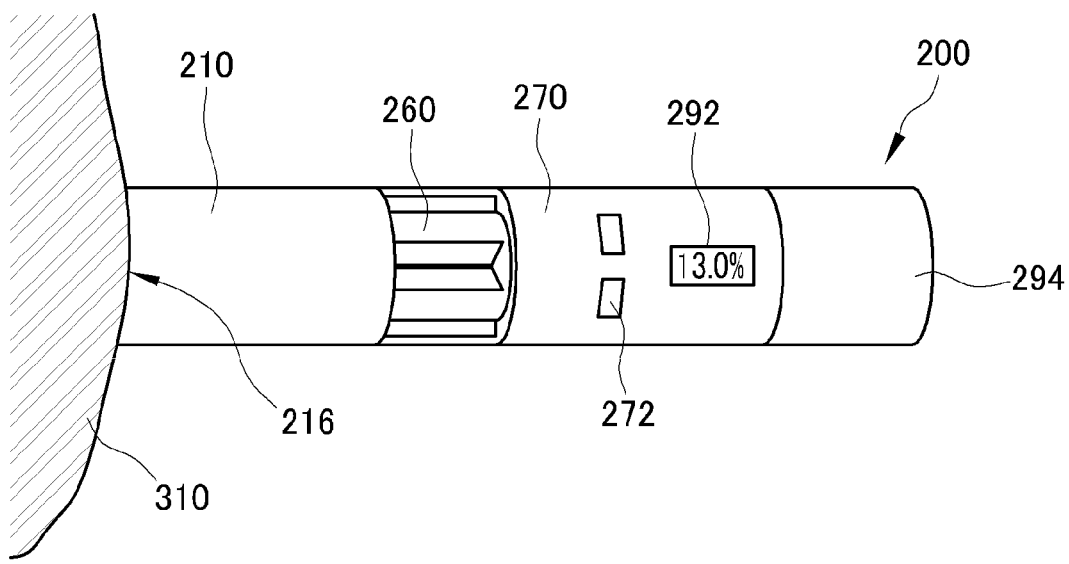
FIG. 3 schematically shows an exterior view of an example skin moisture measuring device attached to skin.

FIG. 2 schematically shows a block diagram of another example skin moisture measuring device configured to measure moisture transpiring from skin, arranged in accordance with at least some embodiments described herein. Also, FIG. 3 schematically shows an exterior view of an example skin moisture measuring device attached to skin, arranged in accordance with at least some embodiments described herein. As depicted, a skin moisture measuring device 200 may include one or more of an elongated enclosure 210, a moisture sensor 220, and/or a cooling unit 240.

In some embodiments, elongated enclosure 210 may have a first end 212 at which an inlet 216 may be arranged. Further, elongated enclosure 210 may have a second end 214 opposite first end 212 at which cooling unit 240 may be arranged. For example, cooling unit 240 may be a thermoelectric cooler, such as Peltier cooler, configured to transfer heat from a second surface 242 of cooling unit 240 facing moisture sensor 220 to a first surface 244 of cooling unit 240 such that second surface 242 becomes cooler than first surface 244. Moisture sensor 220 may be arranged between first end 212 and second end 214 inside elongated enclosure 210. Skin moisture measuring device 200 may further include a first temperature sensor 230 arranged at or proximate moisture sensor 220, and a second temperature sensor 250 arranged at or proximate cooling unit 240.

In some embodiments, skin moisture measuring device 200 may further include a heat sink 260 configured to dissipate heat generated from cooling unit 240. More specifically, one side of heat sink 260 may be attached to first surface 244 of cooling unit 240 opposite to moisture sensor 220, while the other side of heat sink 260 may be coupled to an elongated enclosure 270. A cooling fan 280 may be disposed inside elongated enclosure 270 and configured to be driven by a motor 282 to produce airflow towards heat sink 260. Further, one or more air intakes 272 may be formed on a surface of elongated enclosure 270 proximate cooling fan 280.

In some embodiments, skin moisture measuring device 200 may further include a controller 290 configured to control the operations of electrical and mechanical elements/units of skin moisture measuring device 200, including moisture sensor 220, first temperature sensor 230, cooling unit 240, second temperature sensor 250, cooling fan 280 and/or motor 282, and/or an output unit 292. For example, output unit 292 may be a LCD (liquid crystal display), and may be configured to report the amount of the moisture detected by moisture sensor 220. Skin moisture measuring device 200 may further include a power supply 294 (for example, a rechargeable battery) configured to supply electric power for operating the electrical and mechanical elements/units of skin moisture measuring device 200, including moisture sensor 220, first temperature sensor 230, cooling unit 240, second temperature sensor 250, cooling fan 280 and motor 282, controller 290, and/or output unit 292.

In operation, inlet 216 may be in contact with skin 310 and receive moisture transpiring from skin 310. The moisture transpiring from skin 310 may flow in a direction from skin 310 to cooling unit 240 because there is a temperature gradient between skin 310 and cooling unit 240 which has a lower temperature than skin 310. In the meantime, moisture sensor 220 may detect an amount of the moisture that is flowing through or near moisture sensor 220. Further, cooling unit 240 may cool and condense the moisture that is reaching a surface facing moisture sensor 220.

In some embodiments, a thermoelectric cooler such as a Peltier cooler may be used as cooling unit 240. In this case, while cooling unit 240 is transferring heat from second surface 242 to first surface 244 of cooling unit 240, heat sink 260 may dissipate the heat generated from first surface 244 of cooling unit 240. Also, to further increase the cooling efficiency, cooling fan 280 may produce airflow towards heat sink 260 while air may be introduced from outside of elongated enclosure 270 through air intakes 272.

Further, first temperature sensor 230 may detect a first temperature of an atmosphere adjacent to moisture sensor 220 while second temperature sensor 250 may detect a second temperature of an atmosphere adjacent to cooling unit 240. In response to detecting the first and second temperatures, controller 290 may control cooling unit 240 to maintain a substantially constant temperature difference between the first and second temperatures. The amount of moisture measured by moisture sensor 220 may be reported to a user via output unit 292, which may display the amount of measured moisture changing depending on the rate of moisture transpiration from skin 310.

In some embodiments, the amount of moisture detected by moisture sensor 220 may indicate an extent of moisture loss from skin 310. In some other embodiments, the amount of moisture detected by moisture sensor 220 may indicate a condition of the skin barrier function.

Figure 4:
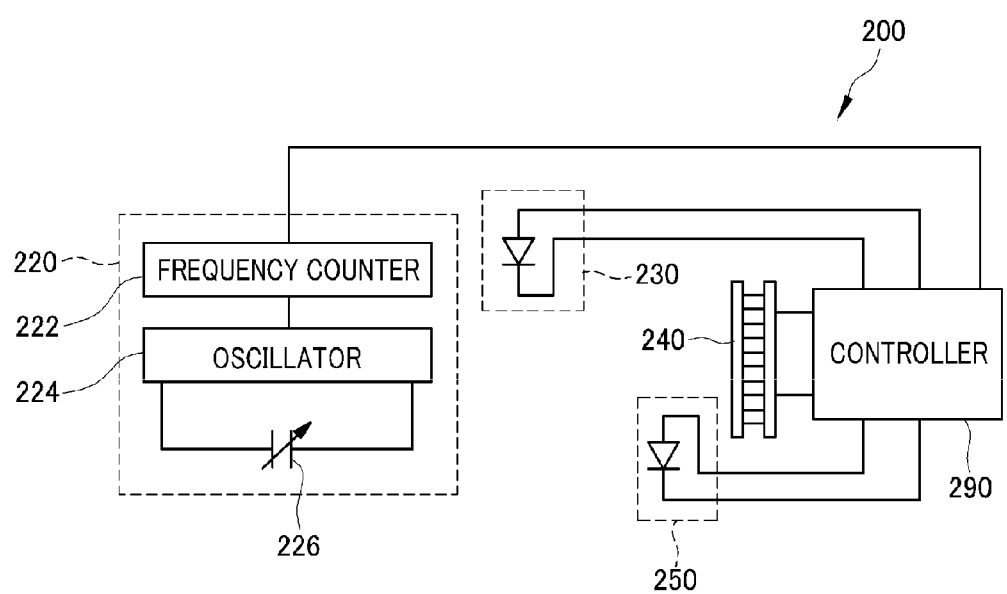
FIG. 4 schematically shows a more detailed block diagram of the example skin moisture measuring device as illustrated in FIG. 2.

FIG. 4 schematically shows a more detailed block diagram of the example skin moisture measuring device as illustrated in FIG. 2, arranged in accordance with at least some embodiments described herein. In particular, FIG. 4 shows a more detailed block diagram of a portion of skin moisture measuring device 200 including moisture sensor 220, first temperature sensor 230, cooling unit 240, second temperature sensor 250, and controller 290.

As illustrated in FIG. 4, moisture sensor 220 may include one or more of a frequency counter 222, an oscillator 224, and/or a capacitor 226. Capacitor 226 may be configured to change capacitance according to the amount of the moisture received by moisture sensor 220. Oscillator 224 may be configured to convert the change of the capacitance into a voltage signal. Further, frequency counter 220 may be configured to determine a frequency of the voltage signal. In some embodiments, moisture sensor 220 may further include a look-up table including a list of humidity rates (or moisture contents) associated with frequencies of voltage signals that are measured for the corresponding humidity rates. Such look-up table may be pre-stored in an internal memory (not shown) of moisture sensor 220.

In operation, moisture sensor 220 may detect an amount of the moisture that is transpiring from skin. More specifically, capacitor 226 may change its capacitance according to the amount of the moisture received by moisture sensor 220. Oscillator 224 may then convert the change of the capacitance into a voltage signal. Further, when frequency counter 220 determines the frequency of the voltage signal, moisture sensor 220 may determine a humidity rate associated with the determined frequency in the look-up table. In the meantime, cooling unit 240 may cool and condense the moisture that is reaching a surface cooling unit 240 facing moisture sensor 220.

Further, first temperature sensor 230 may detect a first temperature of an atmosphere adjacent to moisture sensor 220 while second temperature sensor 250 may detect a second temperature of an atmosphere adjacent to cooling unit 240. The detected first and second temperatures may be transmitted to controller 290. In response to the first and second temperatures, controller 290 may control the cooling efficiency of cooling unit 240, thereby maintaining a substantially constant temperature difference between the first and second temperatures.

Figure 5:
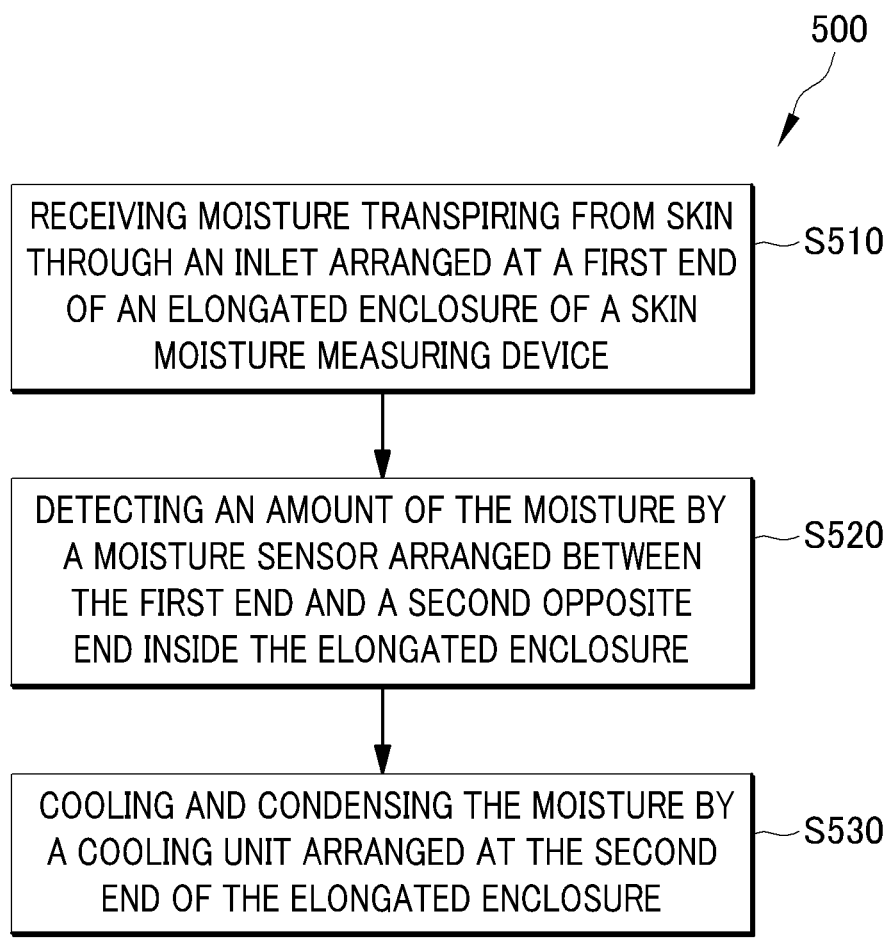
FIG. 5 illustrates an example flow diagram of a method adapted to measure skin moisture.

FIG. 5 illustrates an example flow diagram of a method adapted to measure skin moisture. An example method 500 in FIG. 5 may be implemented using, for example, a computing device including a processor adapted to measure moisture in skin.

Method 500 may include one or more operations, actions, or functions as illustrated by one or more of blocks S510, S520, and/or S530. Although illustrated as discrete blocks, various blocks may be divided into additional blocks, combined into fewer blocks, or eliminated, depending on the desired implementation. In some further examples, the various described blocks may be implemented as a parallel process instead of a sequential process, or as a combination thereof. Method 500 may begin at block S510, "RECEIVING MOISTURE TRANSPIRING FROM SKIN THROUGH AN INLET ARRANGED AT A FIRST END OF AN ELONGATED ENCLOSURE OF A SKIN MOISTURE MEASURING DEVICE."

At block S510, moisture transpiring from skin may be received through an inlet arranged at a first end of an elongated enclosure of a skin moisture measuring device. As depicted in FIG. 1, inlet 150 may be arranged at first end 122 of elongated enclosure 120 of skin moisture measuring device 100. Inlet 150 may receive moisture 160 transpiring from skin 110. Moisture 160 transpiring from skin 110 may flow in a direction from skin 110 to cooling unit 140 because there is a temperature gradient between skin 110 and cooling unit 140 which has a lower temperature than skin 110. Block S510 may be followed by block S520, "DETECTING AN AMOUNT OF THE MOISTURE BY A MOISTURE SEN- SOR ARRANGED BETWEEN THE FIRST END AND A SECOND OPPOSITE END INSIDE THE ELONGATED ENCLOSURE."

At block S520, an amount of the moisture may be detected by a moisture sensor arranged between the first end and a second opposite end inside the elongated enclosure. As illustrated in FIG. 1, moisture sensor 130 may be arranged between first end 122 and second end 124 inside elongated enclosure 120. Moisture sensor 130 may detect an amount of moisture 160 that is flowing through or near moisture sensor 130. Block S520 may be followed by block S530, "COOLING AND CONDENSING THE MOISTURE BY A COOLING UNIT ARRANGED AT THE SECOND END OF THE ELONGATED ENCLOSURE."

At block S530, the moisture may be cooled and condensed by a cooling unit arranged at the second end of the elongated enclosure. As illustrated in FIG. 1, cooling unit 140 may be arranged at second end 124 opposite to first end 122 inside elongated enclosure 120. Cooling unit 140 may cool and condense moisture 160 that is reaching a surface of cooling unit 140 facing moisture sensor 130.

In some embodiments, a first temperature of an atmosphere adjacent to the moisture sensor may be detected while a second temperature of an atmosphere adjacent to the cooling unit may be detected. In response to detecting the first and second temperatures, the cooling unit may be controlled by a controller (for example, controller 290 in FIG. 2) to maintain a substantially constant temperature difference between the first and second temperatures. For example, the cooling unit may be a thermoelectric cooler, such as Peltier cooler, configured to transfer heat from a second surface of the cooling unit facing the moisture sensor to a first surface of the cooling unit such that the second surface becomes cooler than the first surface.

In some embodiments, an extent of moisture loss from the skin may be determined from the amount of moisture detected by the moisture sensor. In some other embodiments, a condition of the skin barrier function may be determined from the amount of moisture detected by the moisture sensor.

Figure 6:
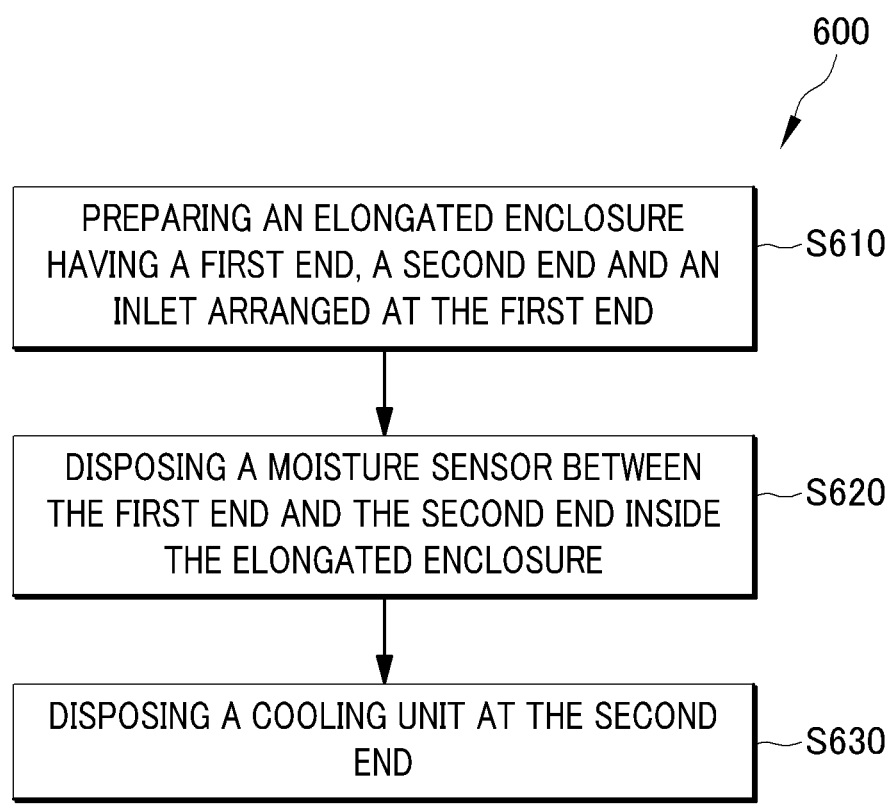
FIG. 6 illustrates an example flow diagram of a method adapted to manufacture a skin moisture measuring device.

FIG. 6 illustrates an example flow diagram of a method adapted to manufacture a skin moisture measuring device, arranged in accordance with at least some embodiments described herein. An example method 600 in FIG. 6 may be implemented using, for example, a computing device including a processor adapted to control manufacturing of a skin moisture measuring device.

Method 600 may include one or more operations, actions, or functions as illustrated by one or more of blocks S610, S620, and/or S630. Although illustrated as discrete blocks, various blocks may be divided into additional blocks, combined into fewer blocks, or eliminated, depending on the desired implementation. In some further examples, the various described blocks may be implemented as a parallel process instead of a sequential process, or as a combination thereof. Method 600 may begin at block S610, "PREPARING AN ELONGATED ENCLOSURE HAVING A FIRST END, A SECOND END AND AN INLET ARRANGED AT THE FIRST END."

At block S610, an elongated enclosure may be prepared to have a first end, a second end and an inlet arranged at the first end. As illustrated in FIGS. 2 and 3, elongated enclosure 210 may be prepared to have first end 212 at which inlet 216 may be arranged, and second end 214 opposite first end 212. Inlet 216 may be configured to be in contact with skin 310 and to receive moisture transpiring from skin 310. Block S610 may be followed by block S620, "DISPOSING A MOISTURE SENSOR BETWEEN THE FIRST END AND THE SECOND END INSIDE THE ELONGATED ENCLOSURE."

At block 620, a moisture sensor may be disposed between the first end and the second end inside the elongated enclosure. As illustrated in FIGS. 2 and 3, moisture sensor 220 may be arranged between first end 212 and second end 214 inside elongated enclosure 210. Moisture sensor 220 may be configured to detect an amount of the moisture that is flowing from skin 310. Block S620 may be followed by block S630, "DISPOSING A COOLING UNIT AT THE SECOND END."

At block 630, a cooling unit may be disposed at the second end. As illustrated in FIGS. 2 and 3, cooling unit 240 may be arranged at second end 214 of elongated enclosure 210. For example, cooling unit 240 may be a thermoelectric cooler, such as Peltier cooler, configured to transfer heat from a second surface 242 of cooling unit 240 facing moisture sensor 220 to a first surface 244 of cooling unit 240 such that second surface 242 becomes cooler than first surface 244.

In some embodiments, a first temperature sensor such as first temperature sensor 230 may be disposed proximate the moisture sensor, where the first temperature sensor may be configured to detect a first temperature of an atmosphere adjacent to the moisture sensor. Also, a second temperature sensor such as second temperature sensor 250 may be disposed proximate the cooling unit, where the second temperature sensor may be configured to detect a second temperature of an atmosphere adjacent to the cooling unit. A controller such as controller 290 may be coupled to the cooling unit, where the controller may be configured to control the cooling unit to maintain a substantially constant temperature difference between the first temperature and the second temperature.

In some embodiments, a heat sink such as heat sink 260 may be attached to a first surface of the cooling unit opposite to the moisture sensor, where the heat sink may be configured to dissipate heat generated from the cooling unit. Further, a cooling fan such as cooling fan 280 may be disposed proximate the heat sink, where the cooling fan may be configured to produce airflow towards the heat sink. Additionally, one or more air intakes such as intakes 272 may be formed on a surface of the elongated enclosure proximate the cooling fan.

In some embodiments, an output unit such as output unit 292 may be disposed on a surface of the elongated enclosure, where the output unit may be configured to report the amount of the moisture detected by the moisture sensor. Additionally, a power supply such as power supply 294 may be coupled to the moisture sensor and the cooling unit, where the power supply may be configured to supply electric power for operating the moisture sensor and the cooling unit.

In light of the present disclosure, one skilled in the art will appreciate that, for this and other methods disclosed herein, the functions performed in the methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Figure 7:
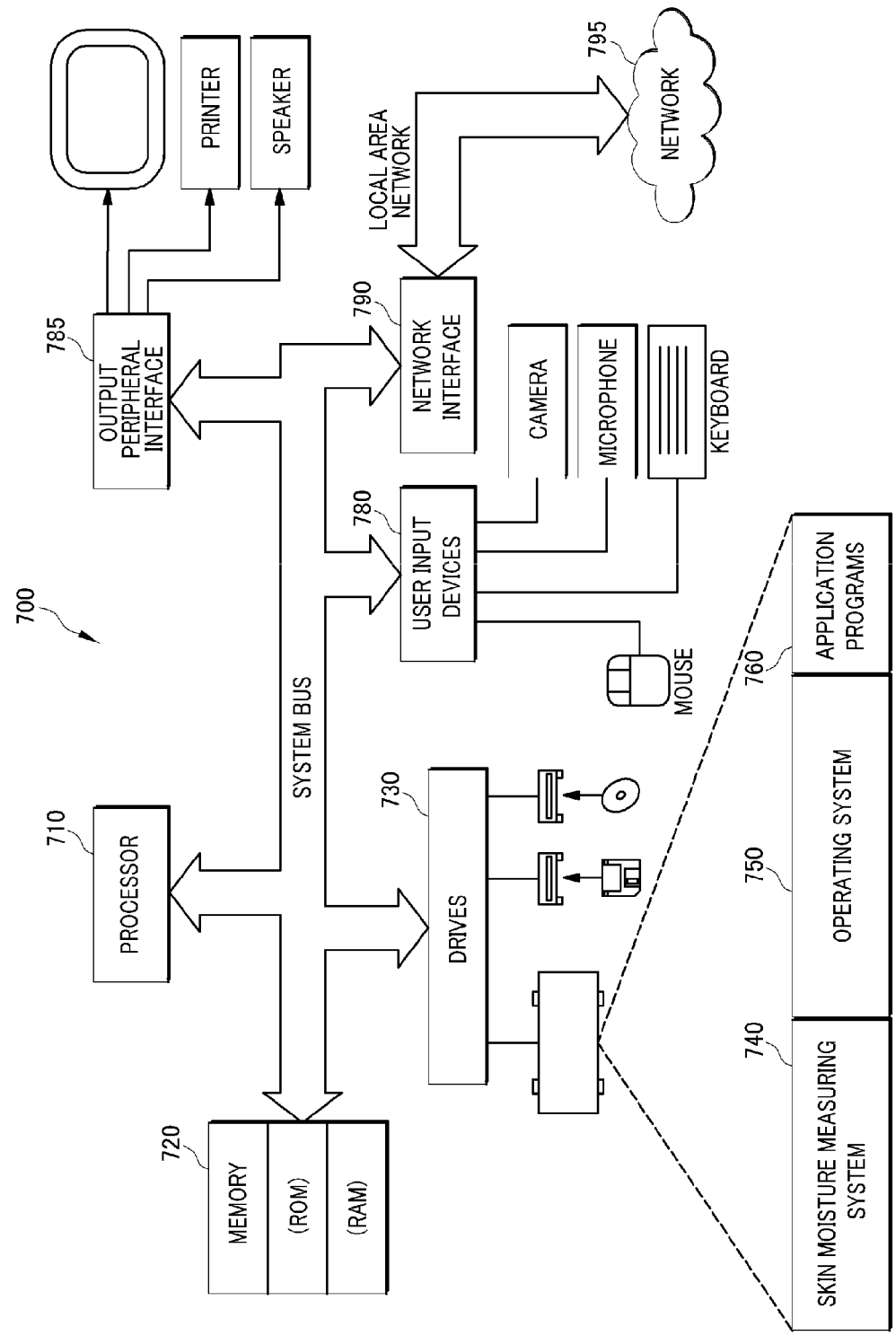
FIG. 7 shows a schematic block diagram illustrating an example computing system that can be configured to implement methods for measuring skin moisture.

FIG. 7 shows a schematic block diagram illustrating an example computing system that can be configured to implement methods for measuring skin moisture, arranged in accordance with at least some embodiments described herein. As depicted in FIG. 7, a computer 700 may include a processor 710, a memory 720 and one or more drives 730. Computer 700 may be implemented as a conventional computer system, an embedded control computer, a laptop, or a server computer, a mobile device, a set-top box, a kiosk, a vehicular information system, a mobile telephone, a customized machine, or other hardware platform.

Drives 730 and their associated computer storage media may provide storage of computer readable instructions, data structures, program modules and other data for computer 700. Drives 730 may include a skin moisture measuring system 740, an operating system (OS) 750, and application programs 760. Skin moisture measuring system 740 may be adapted to control a skin moisture measuring device in such a manner as described above with respect to FIGS. 1 to 6.

Computer 700 may further include user input devices 780 through which a user may enter commands and data. Input devices can include an electronic digitizer, a camera, a microphone, a keyboard and pointing device, commonly referred to as a mouse, trackball or touch pad. Other input devices may include a joystick, game pad, satellite dish, scanner, or the like.

These and other input devices can be coupled to processor 710 through a user input interface that is coupled to a system bus, but may be coupled by other interface and bus structures, such as a parallel port, game port or a universal serial bus (USB). Computers such as computer 700 may also include other peripheral output devices such as display devices, which may be coupled through an output peripheral interface 785 or the like.

Computer 700 may operate in a networked environment using logical connections to one or more computers, such as a remote computer coupled to a network interface 790. The remote computer may be a personal computer, a server, a router, a network PC, a peer device or other common network node, and can include many or all of the elements described above relative to computer 700.

Networking environments are commonplace in offices, enterprise-wide area networks (WAN), local area networks (LAN), intranets, and the Internet. When used in a LAN or WLAN networking environment, computer 700 may be coupled to the LAN through network interface 790 or an adapter. When used in a WAN networking environment, computer 700 typically includes a modem or other means for establishing communications over the WAN, such as the Internet or a network 795. The WAN may include the Internet, the illustrated network 795, various other networks, or any combination thereof. It will be appreciated that other mechanisms of establishing a communications link, ring, mesh, bus, cloud, or network between the computers may be used.

In some embodiments, computer 700 may be coupled to a networking environment. Computer 700 may include one or more instances of a physical computer-readable storage medium or media associated with drives 730 or other storage devices. The system bus may enable processor 710 to read code and/or data to/from the computer-readable storage media. The media may represent an apparatus in the form of storage elements that are implemented using any suitable technology, including but not limited to semiconductors, magnetic materials, optical media, electrical storage, electrochemical storage, or any other such storage technology. The media may represent components associated with memory 720, whether characterized as RAM, ROM, flash, or other types of volatile or nonvolatile memory technology. The media may also represent secondary storage, whether implemented as storage drives 730 or otherwise. Hard drive implementations may be characterized as solid state, or may include rotating media storing magnetically encoded information.

Processor 710 may be constructed from any number of transistors or other circuit elements, which may individually or collectively assume any number of states. More specifically, processor 710 may operate as a state machine or finite-state machine. Such a machine may be transformed to a second machine or specific machine by loading executable instructions. These computer-executable instructions may transform processor 710 by specifying how processor 710 transitions between states, thereby transforming the transistors or other circuit elements constituting processor 710 from a first machine to a second machine. The states of either machine may also be transformed by receiving input from user input devices 780, network interface 790, other peripherals, other interfaces, or one or more users or other actors. Either machine may also transform states, or various physical characteristics of various output devices such as printers, speakers, video displays, or otherwise.

Figure 8:
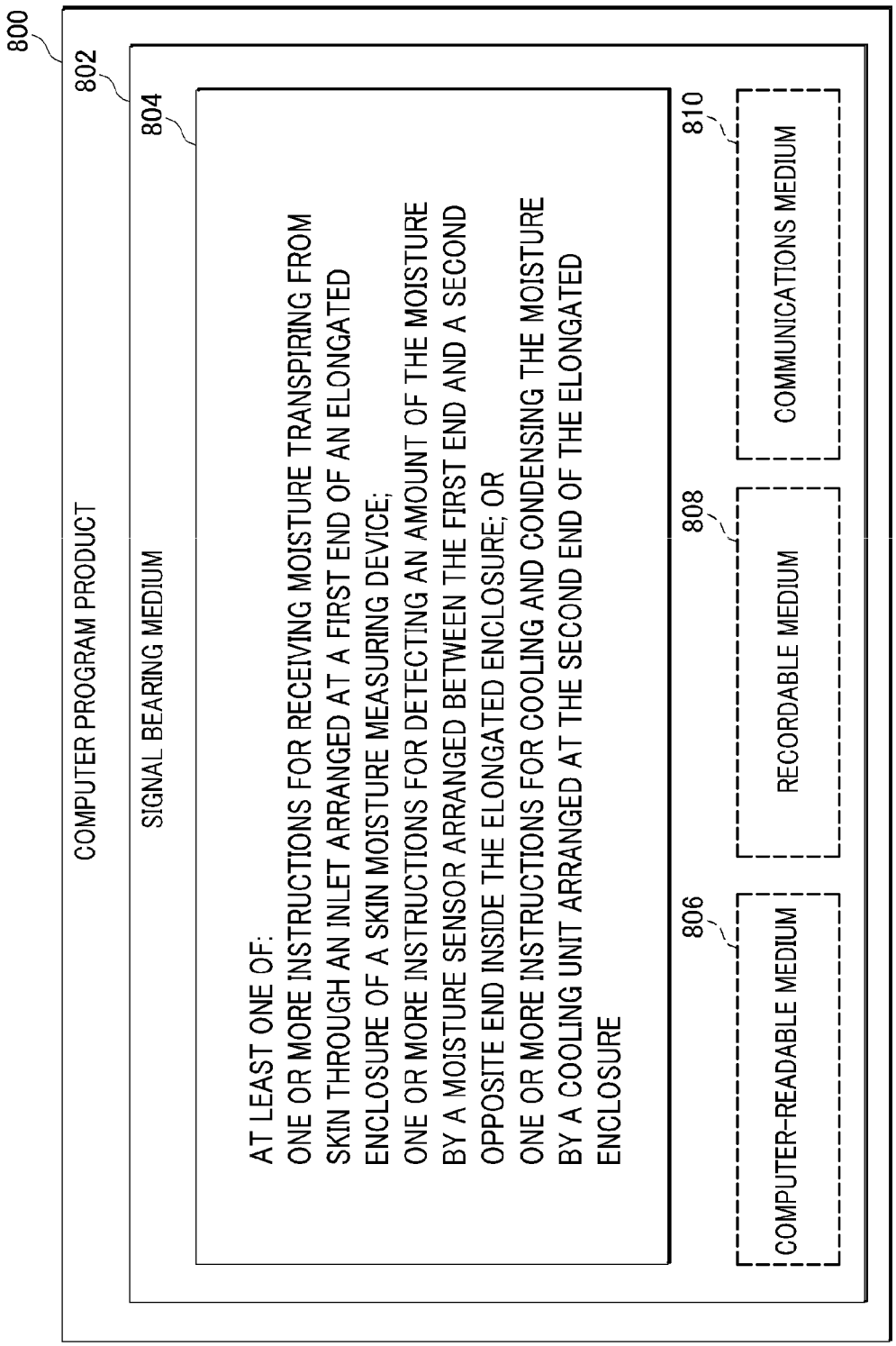
FIG. 8 illustrates computer program products that can be utilized to measure skin moisture.

FIG. 8 illustrates computer program products that can be utilized to measure skin moisture, in accordance with at least some embodiments described herein. Program product 800 may include a signal bearing medium 802. Signal bearing medium 802 may include one or more instructions 804 that, when executed by, for example, a processor, may provide the functionality described above with respect to FIGS. 1 to 6. By way of example, instructions 804 may include at least one of: one or more instructions for receiving moisture transpiring from skin through an inlet arranged at a first end of an elongated enclosure of a skin moisture measuring device; one or more instructions for detecting an amount of the moisture by a moisture sensor arranged between the first end and a second opposite end inside the elongated enclosure; or one or more instructions for cooling and condensing the moisture by a cooling unit arranged at the second end of the elongated enclosure. Thus, for example, referring to FIGS. 1 to 4, skin moisture measuring device 100 or 200 may undertake one or more of the blocks shown in FIG. 5 in response to instructions 804.

In some implementations, signal bearing medium 802 may encompass a computer-readable medium 806, such as, but not limited to, a hard disk drive, a Compact Disc (CD), a Digital Video Disk (DVD), a digital tape, memory, etc. In some implementations, signal bearing medium 802 may encompass a recordable medium 808, such as, but not limited to, memory, read/write (R/W) CDs, R/W DVDs, etc. In some implementations, signal bearing medium 802 may encompass a communications medium 810, such as, but not limited to, a digital and/or an analog communication medium (for example, a fiber optic cable, a waveguide, a wired communications link, a wireless communication link, etc.). Thus, for example, program product 800 may be conveyed to one or more modules of skin moisture measuring device 100 or 200 by an RF signal bearing medium 802, where the signal bearing medium 802 is conveyed by a wireless communications medium 810 (for example, a wireless communications medium conforming with the IEEE 802.11 standard).

EXAMPLES

The present disclosure will be understood more readily by reference to the following examples, which are provided by way of illustration and are not intended to be limiting in any way.

Example 1: Construction of a Skin Moisture Measuring Device

Figure 9A:
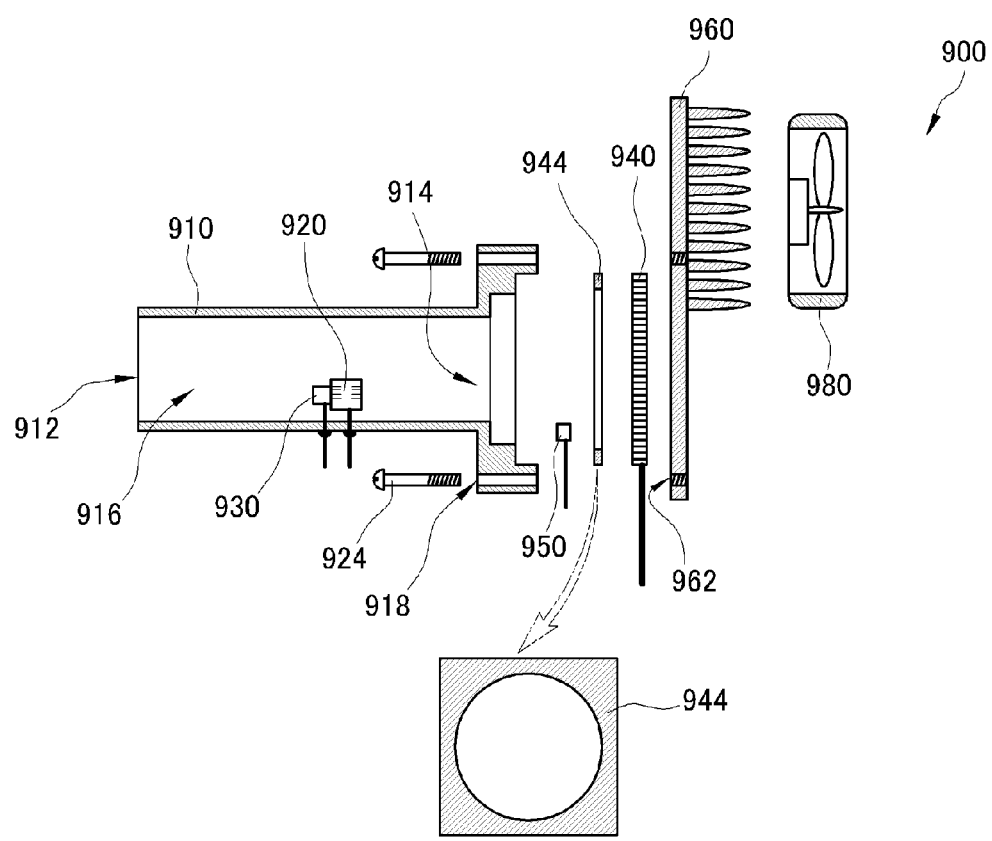
FIG. 9A illustrates elements or parts of an example skin moisture measuring device in a disassembled state, configured to measure moisture transpiring from skin.

In one experimental example, a skin moisture measuring device was constructed in accordance with the above embodiments. FIG. 9A illustrates elements or parts of an example skin moisture measuring device in a disassembled state, configured to measure moisture transpiring from skin, arranged in accordance with at least some embodiments described herein. All elements or parts that are illustrated in FIG. 9A and will be described below may have similar configurations and/or functions to corresponding elements/parts of skin moisture measuring device 100 or 200.

An elongated enclosure 910 made of acrylic resin was prepared. Elongated enclosure 910 have a first end 912, at which an inlet 916 is arranged, and a second end 914 opposite first end 912 at which cooling unit 940 (for example, Peltier cooler) is to be arranged. Moisture sensor 920 was arranged between first end 912 and second end 914 inside elongated enclosure 910. Further, a first temperature sensor 930 was arranged proximate moisture sensor 920.

Elongated enclosure 910 was then attached to a heat sink 960 with cooling unit 940 interposed between elongated enclosure 910 and heat sink 960, by fastening screws 924 (or bolts) through holes 918 (formed in second end 914) and holes 962 (formed in heat sink 960). To air-tightly attach elongated enclosure 910 to heat sink 960, sealing member 944 made of silicon elastomeric material was interposed between second end 914 of elongated enclosure 910 and cooling unit 940. Further, a second temperature sensor 950 was arranged on one side of sealing member 944 opposing to cooling unit 940. Finally, a cooling fan 980 was disposed to produce airflow towards heat sink 960.

Figure 9B:
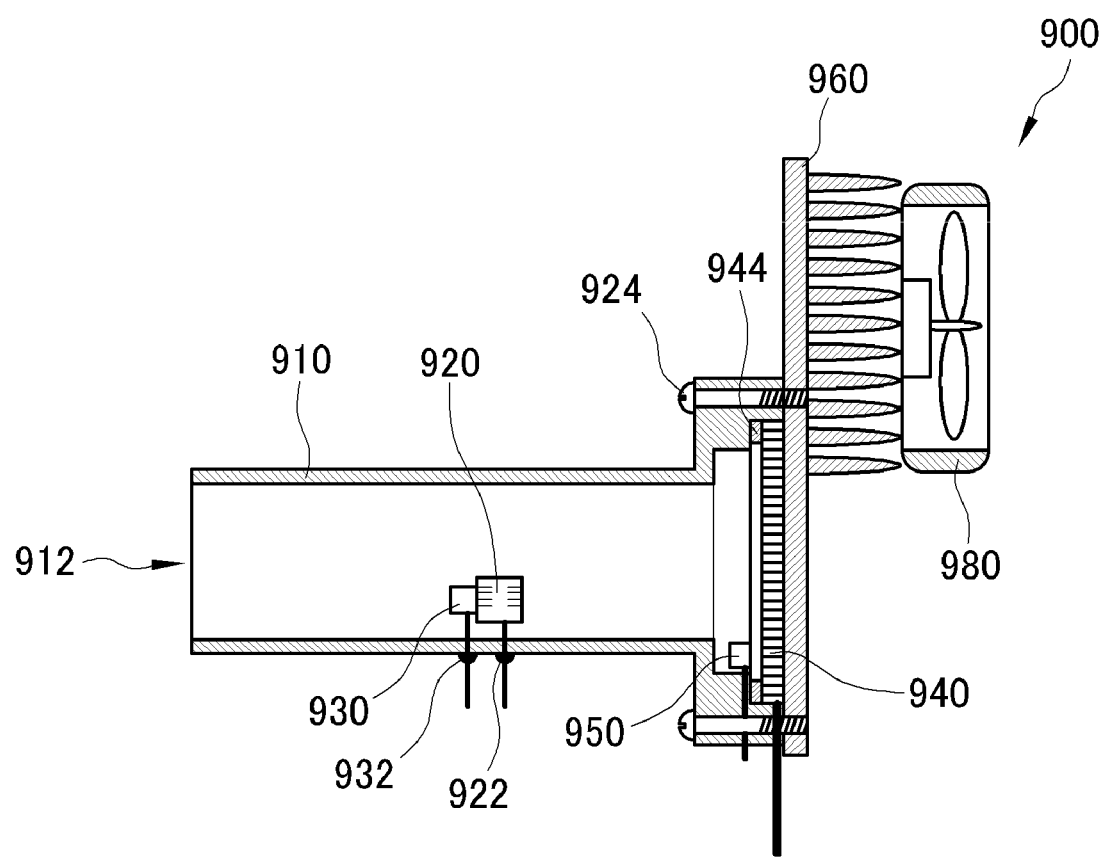
FIG. 9B illustrates an example skin moisture measuring device assembled from the elements or parts in FIG. 9A, configured to measure moisture transpiring from skin.

FIG. 9B illustrates an example skin moisture measuring device, assembled from the elements or parts in FIG. 9A, configured to measure moisture transpiring from skin, arranged in accordance with at least some embodiments described herein. More specifically, FIG. 9B shows the a skin moisture measuring device 900 that was assembled in the manner as described above with reference to FIG. 9A.

After assembling the parts or elements of skin moisture measuring device 900, wires for electrical connecting between sensors 920, 930 and 950 and cooling unit 940 and a controller and a power supply (not shown) were installed through holes on the side surface of elongated enclosure 910. Further, epoxy resins 922 and 932 were additionally disposed to fix wires from sensors 920 and 930 to the side surface of elongated enclosure 910.

Example 2: Using a Skin Moisture Measuring Device to Measure Moisture Content of Dry and Hydrated Skins In one experimental example, the humidity (or moisture content) of some parts of human body was measured by using a skin moisture measuring device manufactured according to the above embodiments. FIGS. 10A to 10D illustrate graphs showing humidity of cheek, palm, forehead, and polyethylene film, respectively, which were measured by a skin moisture measuring device, arranged in accordance with at least some embodiments described herein.

In this example, a skin moisture measuring device was implemented according to the configuration as illustrated in FIGS. 1 to 4 and 9A and 9B. The moisture measurement was conducted for about 60 seconds for each of cheek, palm, forehead and polyethylene film in an environment having a temperature of 26 degrees Celsius and a humidity of 60%. Also, a cooling unit of the skin moisture measuring device was controlled, such that the difference between the first and second temperatures (measured by first and second temperature sensors) was maintained to be about 10 degrees Celsius.

Figure 10A:
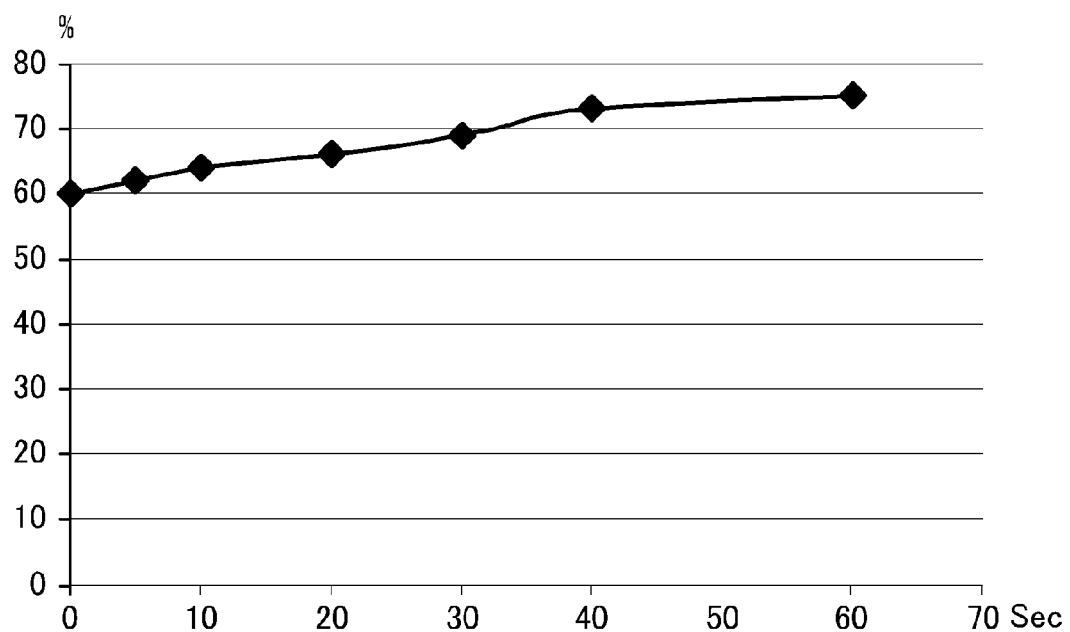
FIGS. 10A to 10D illustrate graphs showing humidity of cheek, palm, forehead and polyethylene film, respectively, which were measured by a skin moisture measuring device.
Figure 10B:
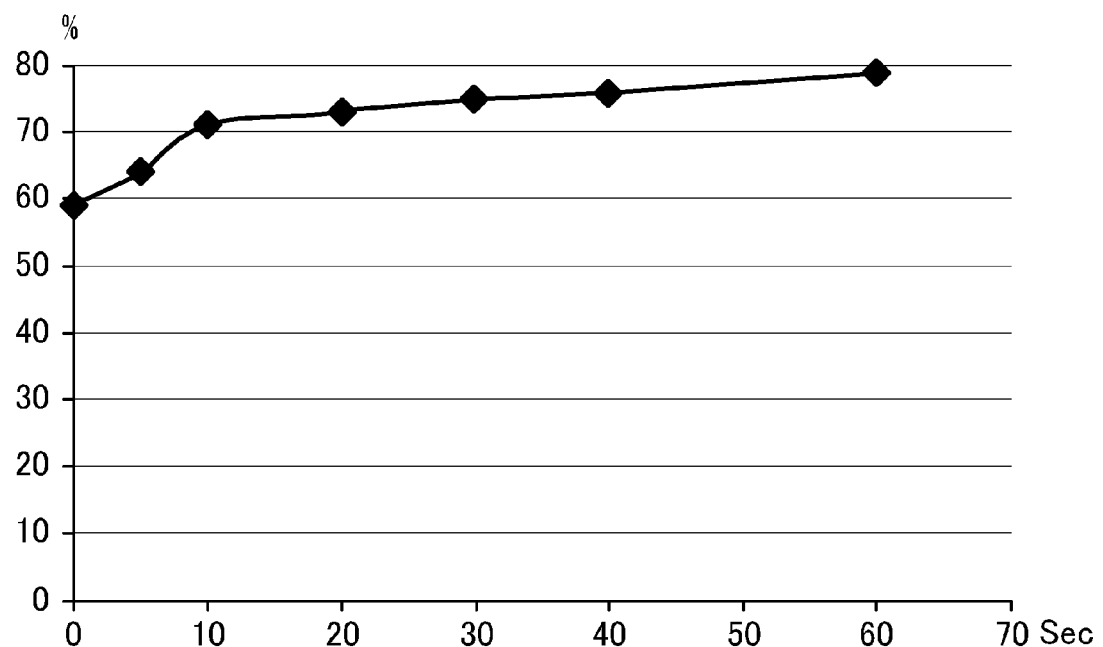

As shown in FIGS. 10A and 10B, the moisture contents measured on the cheek and the palm were increased in a substantially constant manner during the measurement period (which was about 60 seconds). It is assumed from the measured data that the moisture transpired from the cheek and palm at a considerable rate, and thus, the transpiration rate exceeded the rate of moisture condensation by the cooling unit.

Figure 10C:
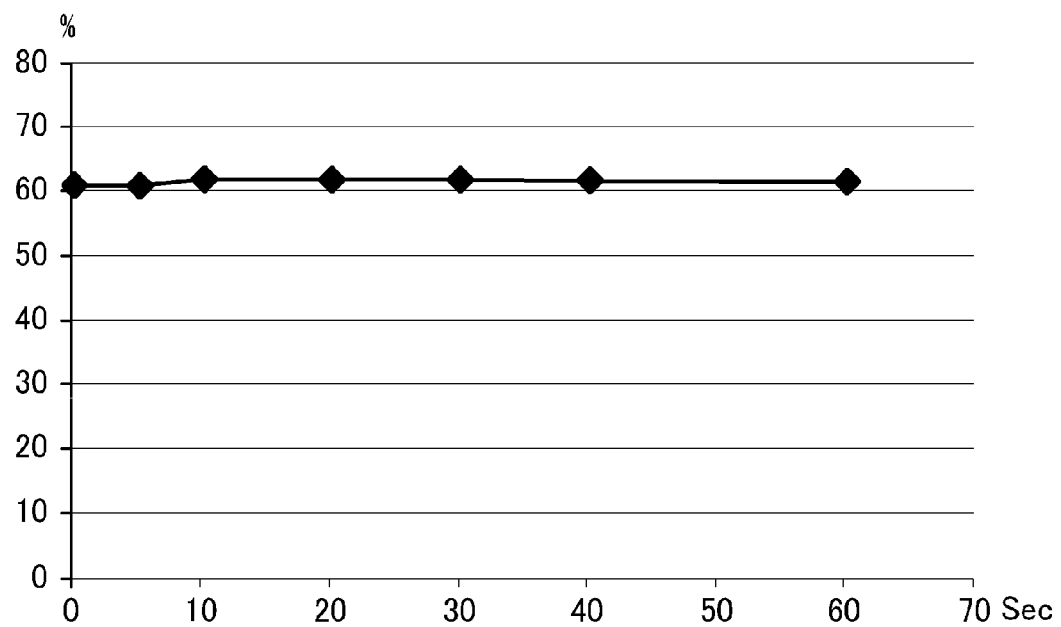

On the other hand, as illustrated in FIG. 10C, the moisture content measured on the forehead stayed at a value slightly greater than 60% during the measurement period. This may show that the transpiration rate at the forehead was significantly lower than the other parts of human body (for example, cheek and palm), which is presumably due to the oil covering the forehead that prevents the moisture from transpiring from the forehead.

Figure 10D:
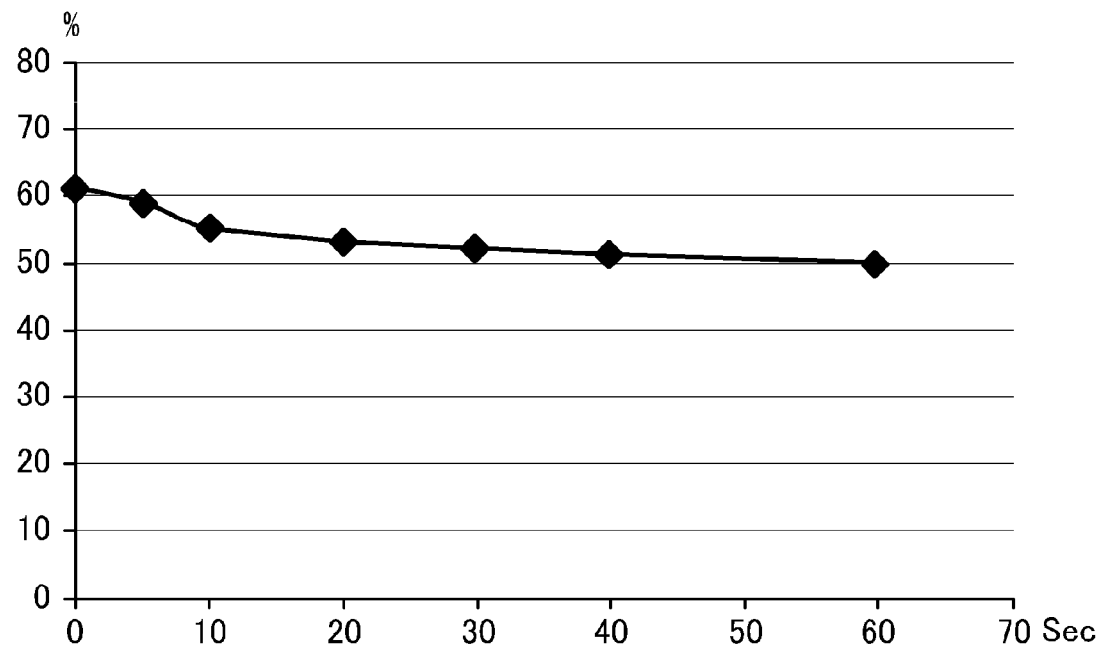

Further, FIG. 10D illustrates a graph showing moisture content measured by the skin moisture measuring device when an inlet of the skin moisture measuring device was air-tightly covered by a polyethylene film. In this case, no moisture transpired from the polyethylene film, while the moisture remaining inside an enclosure of the skin moisture measuring device continued to be condensed by the cooling unit. Accordingly, as illustrated, the measured moisture content was gradually decreased from about 60% to about 50% during the measurement period.

In another experimental example, the humidity (or moisture content) of cheek and forehead in dry and normal conditions was measured by using a skin moisture measuring device manufactured according to the above embodiments. FIGS. 11A to 11D illustrate graphs showing humidity of cheek and forehead in dry and normal conditions, respectively, which were measured by a skin moisture measuring device, arranged in accordance with at least some embodiments described herein.

In this example, the moisture measurement was conducted for about 60 seconds for each of cheek and forehead in dry condition (for example, in an environment having a temperature of 21 degrees Celsius and a humidity of 45%) and normal condition (for example, in an environment having a temperature of 21 degrees Celsius and a humidity of 51%). Also, a cooling unit of the skin moisture measuring device was controlled, such that the difference between the first and second temperatures (measured by first and second temperature sensors) was maintained to be about 10 degrees Celsius.

As shown in FIGS. 11A and 11B, the moisture contents measured on the cheek and the forehead in dry condition were quickly increased in an early stage of the measurement period (which was about 60 seconds) and slowly increase in its later stage. It is assumed from the measured data that the moisture transpired from the cheek and forehead at a considerable rate in dry condition, and thus, the transpiration rate exceeded the rate of moisture condensation by the cooling unit.

Figure 11C:
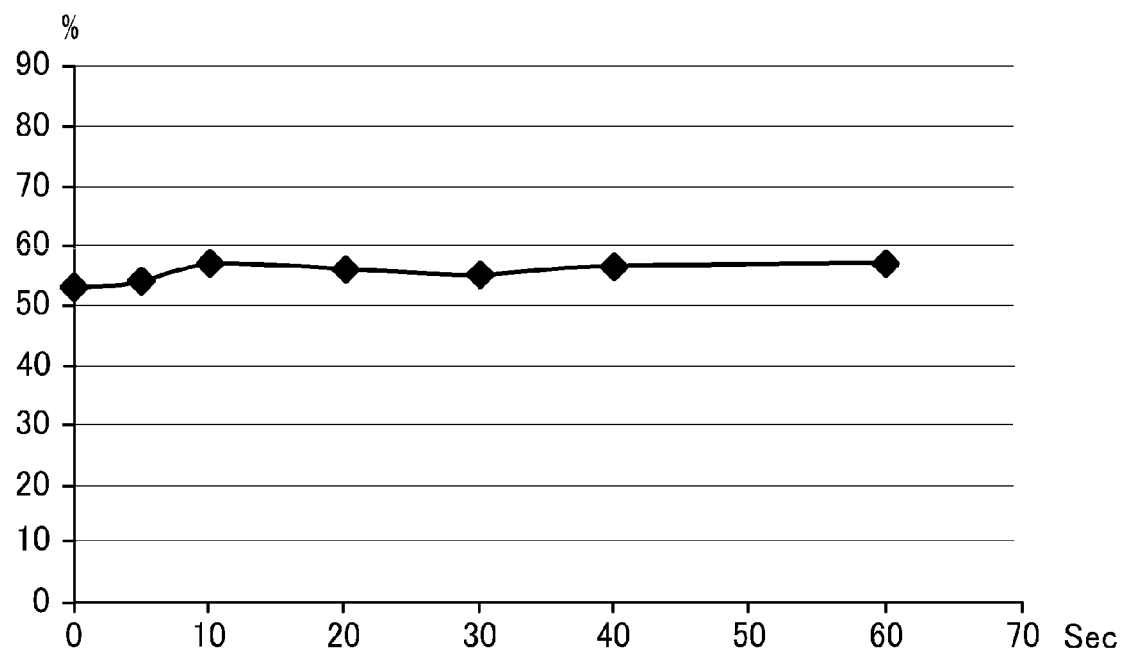
Figure 11D:
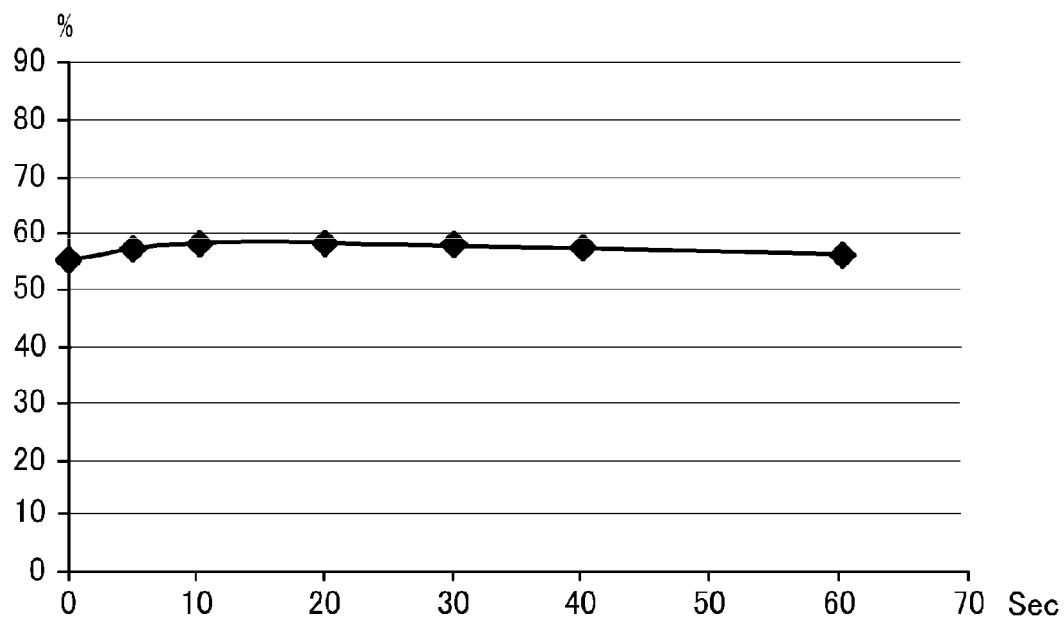

On the other hand, as illustrated in FIGS. 11C and 11D, the moisture content measured on the cheek and forehead in normal condition stayed at a value within a range of 50% to 60% during the measurement period. This may show that the transpiration rate in normal condition was significantly lower than that in dry condition.

As described above, skin moisture measuring devices according to some embodiments of the present disclosure can be manufactured in a portable size for individual users in a cost-effective manner compared to conventional skin moisture measuring devices. Further, contrary to the conventional device conducting capacitance measurement using electrodes or probes attached to skin, the skin moisture measuring devices according to the present disclosure can decrease stress on the skin because they do not require any electrodes or probes to be attached to skin. Further, the skin moisture measuring devices according to the present disclosure can measure moisture transpiring from a wide area of skin whereas the conventional device may require a plurality of electrodes or probes to detect moisture in such case.

The present disclosure is not to be limited in terms of the particular embodiments described in this application, which are intended as illustrations of various aspects. Many modifications and variations may be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely examples and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A skin moisture measuring device, comprising:
an elongated enclosure having a first end and a second end;
an inlet arranged at the first end, configured to be in contact with skin and to receive moisture transpiring from the skin;
a moisture sensor arranged between the first end and the second end inside the elongated enclosure, configured to detect an amount of the moisture, wherein the moisture sensor comprises:
a capacitor configured to change capacitance according to the amount of the moisture;
an oscillator configured to convert the change of the capacitance into a voltage signal;
a frequency counter configured to determine a frequency of the voltage signal; and
a lookup table comprising a list of moisture contents associated with a list of frequencies of voltage signals that are measured for the corresponding moisture contents; and
a cooling unit arranged at the second end, configured to cool and condense the moisture.

2. The device of claim 1, further comprising:
a first temperature sensor arranged proximate the moisture sensor, configured to detect a first temperature of an atmosphere adjacent to the moisture sensor;
a second temperature sensor arranged proximate the cooling unit, configured to detect a second temperature of an atmosphere adjacent to the cooling unit; and
a controller configured to control the cooling unit to maintain a substantially constant temperature difference between the first temperature and the second temperature.

3. The device of claim 1, further comprising:
a heat sink attached to a first surface of the cooling unit opposite to the moisture sensor,
wherein the heat sink is configured to dissipate heat generated from the cooling unit.

4. The device of claim 3, further comprising:
a cooling fan configured to produce airflow towards the heat sink.

5. The device of claim 4, further comprising:
one or more air intakes formed on a surface of the elongated enclosure proximate the cooling fan.

6. The device of claim 1, further comprising:
an output unit configured to report the amount of the moisture detected by the moisture sensor.

7. The device of claim 1, wherein the amount of moisture detected by the moisture sensor indicates an extent of moisture loss from the skin.

8. The device of claim 1, wherein the amount of moisture detected by the moisture sensor indicates a condition of the skin barrier function.

9. The device of claim 1, wherein the cooling unit is a thermoelectric cooler configured to transfer heat from a second surface of the cooling unit facing the moisture sensor to a first surface of the cooling unit such that the second surface becomes cooler than the first surface.

10. The device of claim 1, further comprising:
a power supply configured to supply electric power for operating the moisture sensor and the cooling unit.

11. A method of measuring skin moisture, the method comprising:
receiving moisture transpiring from skin through an inlet arranged at a first end of an elongated enclosure of a skin moisture measuring device;
detecting an amount of the moisture by a moisture sensor arranged between the first end and a second opposite end inside the elongated enclosure;
changing a capacitance of the amount of detected moisture by a capacitor;
converting the change of the capacitance into a voltage signal by an oscillator;
determining a frequency of the voltage signal by a frequency counter;
determining the skin moisture by accessing a lookup table comprising a list of moisture contents associated with a list of frequencies of voltage signals that are measured for the corresponding moisture contents; and
cooling and condensing the moisture by a cooling unit arranged at the second end of the elongated enclosure.

12. The method of claim 11, further comprising:
detecting a first temperature of an atmosphere adjacent to the moisture sensor by a first temperature sensor arranged proximate the moisture sensor;
detecting a second temperature of an atmosphere adjacent to the cooling unit by a second temperature sensor arranged proximate the cooling unit; and
controlling, by a controller, the cooling unit to maintain a substantially constant temperature difference between the first temperature and the second temperature.

13. The method of claim 11, further comprising:
dissipating heat generated from the cooling unit by a heat sink attached to a first surface of the cooling unit opposite to the moisture sensor.

14. The method of claim 13, further comprising:
producing an airflow towards the heat sink by a cooling fan.

15. The method of claim 11, further comprising:
reporting, by an output unit, the amount of the moisture detected by the moisture sensor.

16. The method of claim 11, further comprising determining an extent of moisture loss from the skin from the amount of moisture detected by the moisture sensor.

17. The method of claim 11, further comprising determining a condition of the skin barrier function from the amount of moisture detected by the moisture sensor.

18. The method of claim 11, wherein cooling and condensing the moisture comprises transferring, by a thermoelectric cooler, heat from a second surface of the cooling unit facing the moisture sensor to a first surface of the cooling unit such that the second surface becomes cooler than the first surface.

19. A non-transitory computer-readable storage medium which stores a program operable by a skin moisture measuring device, the program comprising one or more instructions for:
obtaining moisture transpiring from skin through an inlet arranged at a first end of an elongated enclosure of a skin moisture measuring device;
detecting an amount of the moisture by a moisture sensor arranged between the first end and a second opposite end inside the elongated enclosure;
changing a capacitance of the amount of detected moisture by a capacitor;

converting the change of the capacitance into a voltage signal by an oscillator;

determining a frequency of the voltage signal by a frequency counter;

determining the skin moisture by accessing a lookup table comprising a list of moisture contents associated with a list of frequencies of voltage signals that are measured for the corresponding moisture contents; and cooling and condensing the moisture by a cooling unit arranged at the second end of the elongated enclosure.

20. A method of manufacturing a skin moisture measuring device, the method comprising:

preparing an elongated enclosure having a first end, a second end and an inlet arranged at the first end, the inlet configured to be in contact with skin and to receive moisture transpiring from the skin;

disposing a moisture sensor between the first end and the second end inside the elongated enclosure, the moisture sensor configured to detect an amount of the moisture;

storing a lookup table comprising a list of moisture contents associated with the frequencies of voltage signal that are measured for the corresponding moisture contents in an internal memory of the moisture sensor; and disposing a cooling unit at the second end, the cooling unit configured to cool and condense the moisture.

21. The method of claim 20, further comprising:

disposing a first temperature sensor proximate the moisture sensor, the first temperature sensor configured to detect a first temperature of an atmosphere adjacent to the moisture sensor;

disposing a second temperature sensor proximate the cooling unit, the second temperature sensor configured to detect a second temperature of an atmosphere adjacent to the cooling unit; and coupling a controller to the cooling unit, the controller configured to control the cooling unit to maintain a substantially constant temperature difference between the first temperature and the second temperature.

22. The method of claim 20, further comprising attaching a heat sink to a first surface of the cooling unit opposite to the moisture sensor, wherein the heat sink is configured to dissipate heat generated from the cooling unit.

23. The method of claim 22, further comprising disposing a cooling fan proximate the heat sink, wherein the cooling fan is configured to produce airflow towards the heat sink.

24. The method of claim 23, further comprising forming one or more air intakes on a surface of the elongated enclosure proximate the cooling fan.

25. The method of claim 20, further comprising disposing an output unit on a surface of the elongated enclosure, wherein the output unit is configured to report the amount of the moisture detected by the moisture sensor.

26. The method of claim 20, further comprising coupling a power supply to the moisture sensor and the cooling unit, wherein the power supply is configured to supply electric power for operating the moisture sensor and the cooling unit.

* * * * *

UNITED STATES PATENT AND TRADEMARK OFFICE
CERTIFICATE OF CORRECTION

PATENT NO. : 9,907,506 B2  
APPLICATION NO. : 14/284579  
DATED : March 6, 2018  
INVENTOR(S) : Mihara Page 1 of 1

It is certified that error appears in the above-identified patent and that said Letters Patent is hereby corrected as shown below:

In the Specification

In Column 10, Line 24, delete "Program product 800" and insert -- Computer program product 800 --, therefor.

In Column 10, Line 44, delete "a hard disk drive," and insert -- a Hard Disk Drive (HDD), --, therefor.

In Column 10, Line 53, delete "wired communications" and insert -- wired communication --, therefor.

In Column 10, Line 54, delete "program product 800" and insert -- computer program product 800 --, therefor.

In Column 14, Line 4, delete "recitation" and insert -- recitation, --, therefor.

In Column 14, Line 26, delete "general" and insert -- general, --, therefor.

In Column 14, Line 34, delete "general" and insert -- general, --, therefor.

Signed and Sealed this  
Nineteenth Day of June, 2018

Andrei Iancu  
*Director of the United States Patent and Trademark Office*